United States Patent
Chiba et al.

(10) Patent No.: US 8,446,147 B2
(45) Date of Patent: May 21, 2013

(54) POSITION DETECTING DEVICE HAVING OPPOSITE-PHASE MAGNETIC-FIELD GENERATING COIL, MEDICAL DEVICE GUIDING SYSTEM, POSITION DETECTING METHOD, AND MEDICAL DEVICE GUIDING METHOD

(75) Inventors: Atsushi Chiba, Tokyo (JP); Akio Uchiyama, Tokyo (JP); Atsushi Kimura, Tokyo (JP); Ryoji Sato, Tokyo (JP)

(73) Assignee: Olympus Medical Systems Corp., Tokyo (JP)

( * ) Notice: Subject to any disclaimer, the term of this patent is extended or adjusted under 35 U.S.C. 154(b) by 846 days.

(21) Appl. No.: 12/595,400

(22) PCT Filed: Apr. 18, 2008

(86) PCT No.: PCT/JP2008/057586
§ 371 (c)(1),
(2), (4) Date: Oct. 9, 2009

(87) PCT Pub. No.: WO2008/136281
PCT Pub. Date: Nov. 13, 2008

(65) Prior Publication Data
US 2010/0134096 A1  Jun. 3, 2010

(30) Foreign Application Priority Data

Apr. 27, 2007 (JP) .................................. 2007-118133

(51) Int. Cl.
*G01B 7/14* (2006.01)
*A61B 5/05* (2006.01)

(52) U.S. Cl.
USPC ................. 324/207.15; 324/207.12; 600/424; 600/420; 600/422; 600/409; 600/117

(58) Field of Classification Search
USPC ............ 324/207.15, 207.12, 207.26, 207.17, 324/207.16; 600/117, 409, 420, 422, 424
See application file for complete search history.

(56) References Cited

U.S. PATENT DOCUMENTS

| 7,751,866 B2 * | 7/2010 | Aoki et al. ..................... 600/424 |
| 8,140,145 B2 * | 3/2012 | Kimura et al. ................. 600/424 |
| 2008/0139883 A1 * | 6/2008 | Uchiyama ..................... 600/117 |
| 2009/0018434 A1 | 1/2009 | Kimura et al. |

FOREIGN PATENT DOCUMENTS

| JP | 2006-026391 | 2/2006 |
| JP | 2007-054246 | 3/2007 |
| WO | WO 2005/120345 A2 | 12/2005 |
| WO | WO 2007/023716 A1 | 3/2007 |

* cited by examiner

*Primary Examiner* — Jay Patidar
(74) *Attorney, Agent, or Firm* — Scully, Scott, Murphy & Presser, P.C.

(57) ABSTRACT

Provided is a position detecting device including a first magnetic-field generating unit including at least one magnetic-field generating coil and that generates a first magnetic field in a detection space where a detected object provided with a circuit including at least one built-in coil is disposed; a magnetic-field detecting unit having a plurality of detecting coils arrayed to detect an induced magnetic field generated from the built-in coil by the generated first magnetic field; and a second magnetic-field generating unit including at least one magnetic-field generating coil, that generates a second magnetic field, and including a magnetic-field component having a phase substantially opposite to the first magnetic field and entering the detecting coils, wherein the first magnetic-field generating unit and the detecting coils are disposed so that a generating direction of the first magnetic field and a detecting direction of the induced magnetic field intersect each other.

42 Claims, 13 Drawing Sheets

POSITION DETECTING DEVICE HAVING OPPOSITE-PHASE MAGNETIC-FIELD GENERATING COIL, MEDICAL DEVICE GUIDING SYSTEM, POSITION DETECTING METHOD, AND MEDICAL DEVICE GUIDING METHOD

TECHNICAL FIELD

The present invention relates to a position detecting device, a medical device guiding system, a position detecting method, and a medical device guiding method.

BACKGROUND ART

Recently, research and development are underway to enable practical use of capsule medical devices (detected objects), such as a swallowable capsule endoscope that is swallowed by a subject or the like and passed through a body cavity tract so that an image inside the body cavity tract at a target site can be acquired.

In order to guide such a capsule medical device to a designated location inside a body cavity tract, it is necessary to precisely detect the position of the capsule medical device inside the body cavity tract.

As a position detecting device for precisely detecting the position of a capsule medical device in a body cavity tract, a position detecting device is known in which a magnetic field is applied from the outside of a subject or the like and in which an induced magnetic field generated from a built-in coil installed in a detected object is detected by an external magnetic sensor (e.g., see Patent Document 1).

The position detecting device disclosed in Patent Document 1 includes a first magnetic-field generating unit having a pair of Helmholtz magnetic-field generating coils disposed opposing each other on either side of a detection space where a subject is disposed, a magnetic-field detecting unit having a plurality of detecting coils arrayed so that their detecting direction substantially coincides with the direction of a first magnetic field generated by the first magnetic-field generating unit, and a second magnetic-field generating unit that generates a second magnetic field having a phase substantially opposite to the first magnetic field.

According to the position detecting device in Patent Document 1, it is possible to dispose the second magnetic-field generating unit in proximity to the magnetic-field detecting unit so that the second magnetic field generated by the second magnetic-field generating unit cancels out the first magnetic field entering the magnetic-field detecting unit from the first magnetic-field generating unit. As a result, the induced magnetic field generated from the built-in coil in the capsule medical device can be detected prominently by the magnetic-field detecting unit, so that there is an advantage that the precision of position detection of the capsule medical device can be improved.

Patent Document 1: Japanese Unexamined Patent Application, Publication No. 2007-54246

DISCLOSURE OF INVENTION

In this case, if the direction of the opening of the built-in coil in the detected object perpendicularly intersects the first magnetic field, an induced magnetic field is not generated, thus causing the problem that the detected object is lost from detection. In order to overcome this problem, it is necessary that first magnetic fields can be generated toward the detection space from three mutually intersecting directions not lying in the same single plane so that the direction of the opening of the built-in coil in the detected object does not perpendicularly intersect the first magnetic fields regardless of the orientation of the built-in coil.

However, as disclosed in Patent Document 1, when using three pairs of first and second magnetic-field generating units and a magnetic-field detecting unit, with the magnetic-field generating direction and the detecting direction aligned with each other, it is necessary to dispose the first magnetic-field generating units, the second magnetic-field generating units, and the magnetic-field detecting units so as to surround the entire periphery of a rectangular block-shaped detection space. Therefore, when applied to a detection space that accommodates the entirety of an object to be inspected, such as a subject, the size of the device conceivably increases.

In the case where the size of the device increases, the detection space becomes large and the magnetic-field detecting units become remote from the detected object, so that there is conceivably a disadvantage that detecting coils having a high sensitivity are needed or magnetic-field generating units capable of generating intense and large magnetic fields are needed.

The present invention has been made in view of the situation described above, and it is an object thereof to provide a position detecting device and a medical device guiding system in which it is possible to dispose a magnetic-field detecting unit in proximity to a detected object, so that it is possible to precisely detect the position of the detected object, while reducing the size and cost of the device.

In order to achieve the above object, the present invention provides the following solutions.

A first aspect of the present invention is a position detecting device comprising a first magnetic-field generating unit that includes at least one magnetic-field generating coil and that generates a first magnetic field in a detection space where a detected object provided with a circuit including at least one built-in coil is disposed; a magnetic-field detecting unit having a plurality of detecting coils arrayed to detect an induced magnetic field generated from the built-in coil by the first magnetic field generated by the first magnetic-field generating unit; and a second magnetic-field generating unit that includes at least one magnetic-field generating coil and that generates a second magnetic field and that includes a magnetic-field component having a phase substantially opposite to the first magnetic field generated by the first magnetic-field generating unit and entering the detecting coils, wherein the first magnetic-field generating unit and the detecting coils are disposed so that a generating direction of the first magnetic field and a detecting direction of the induced magnetic field intersect each other.

According to the first aspect, the first magnetic field entering the detecting coils are canceled by the magnetic-field component of the second magnetic field generated by the second magnetic-field generating unit, which has a phase substantially opposite to the first magnetic field entering the detecting coils. Thus, the induced magnetic field generated from the built-in coil in the detected object becomes prominent, so that precise position detection can be achieved. In this case, by disposing the first magnetic-field generating unit and the detecting coils so that the generating direction of the first magnetic field and the detecting direction of the induced magnetic field intersect each other, it becomes possible with the same single magnetic-field detecting unit to detect induced magnetic fields from the detected object associated with first magnetic fields in a plurality of mutually intersecting directions. As a result, it is not necessary to dispose a magnetic-field detecting unit for each direction of a first magnetic field, and it is possible to detect the induced magnetic fields from the built-in coil associated with the first magnetic fields in the plurality of directions by the single magnetic-field detecting unit disposed at a location closest to the detected object. This serves to prevent an increase in the size of the detection space, and thereby serves to reduce the size and cost of the device.

In the first aspect, preferably, the first magnetic-field generating unit and the detecting coils are disposed so that the generating direction of the first magnetic field and the detecting direction of the induced magnetic field intersect each other substantially perpendicularly.

In the first aspect, the second magnetic-field generating unit may be configured to generate second magnetic fields having different intensities according to positions of the individual detecting coils relative to the first magnetic-field generating unit.

By disposing the first magnetic-field generating unit and the detecting coils so that the generating direction of the first magnetic field and the detecting direction of the induced magnetic field intersect each other, the intensity of the first magnetic field entering the array of the plurality of detecting coils varies according to the positions of the detecting coils. Accordingly, the first magnetic field entering the individual detecting coils at different intensities can be canceled effectively, so that the position of the detected object can be detected more precisely.

Furthermore, in the above configuration, the second magnetic-field generating unit may generate second magnetic fields having different intensities for a plurality of sets of detecting coils that are grouped on the basis of their positions relative to the first magnetic-field generating unit.

Accordingly, detecting coils at which the first magnetic field enters at equivalent intensities are grouped into the same set of detecting coils, and the first magnetic field is canceled by second magnetic fields that are common on a group basis, so that the second magnetic-field generating unit can be simplified.

Alternatively, in the above configuration, the second magnetic-field generating unit may be provided individually for each of the detecting coils.

Accordingly, it is possible to individually and effectively cancel the first magnetic field entering the individual detecting coils at different intensities and in different directions, so that the precision of position detection of the detected object can be improved.

Furthermore, in the first aspect, the at least one magnetic-field generating coil of the first magnetic-field generating unit may be a radial-direction magnetic-field generating coil that is disposed along a substantially cylindrical surface surrounding the detection space and that generates the first magnetic field in one radial direction of the substantially cylindrical surface.

Accordingly, by the operation of the radial-direction magnetic-field generating coil, the first magnetic field is generated in the one radial direction of the substantially cylindrical surface surrounding the detection space, so that the induced magnetic field from the built-in coil in the detected object can be detected precisely by the magnetic-field detecting unit, which has a detecting direction in another radial direction intersecting the first magnetic field. By disposing the radial-direction magnetic-field generating coil of the first magnetic-field generating unit along the substantially cylindrical surface surrounding the detection space, it is possible to dispose the radial-direction magnetic-field generating coil in proximity to and so as not to interfere with an object to be inspected that is accommodated in the detection space, such as a human body.

Furthermore, in the first aspect, the at least one magnetic-field generating coil of the first magnetic-field generating unit may be configured by a first radial-direction magnetic-field generating coil that is disposed along a substantially cylindrical surface surrounding the detection space and that generates the first magnetic field in one radial direction of the substantially cylindrical surface and a second radial-direction magnetic-field generating coil that is disposed along the substantially cylindrical surface and that generates a radial-direction magnetic field in a radial direction of the substantially cylindrical surface, the radial direction intersecting the first magnetic field generated by the first radial-direction magnetic-field generating coil.

Accordingly, by the operation of the first radial-direction magnetic-field generating coil and the second radial-direction magnetic-field generating coil, magnetic fields are generated in the detection space from two radial directions intersecting each other, and induced magnetic fields generated from the built-in coil in the detected object and individually associated with the two radial-direction magnetic fields can be detected precisely by the same single magnetic-field detecting unit.

Furthermore, in the above configuration, the generating direction of the radial-direction magnetic field generated by the second radial-direction magnetic-field generating coil may coincide with the detecting direction of the induced magnetic field by the detecting coils, and the position detecting device may comprise a third magnetic-field generating unit that generates a third magnetic field having a phase substantially opposite to the radial-direction magnetic field generated by the second radial-direction magnetic-field generating coil and entering any of the detecting coils.

Accordingly, the induced magnetic field induced in the built-in coil in the detected object by the radial-direction magnetic field generated by the second radial-direction magnetic-field generating coil is detected by the detecting coils, whose directing direction is the same as the direction of the radial-direction magnetic field. Since the radial-direction magnetic field generated by the second radial-direction magnetic-field generating coil and the third magnetic field having a phase substantially opposite to the radial-direction magnetic field enter the detecting coils, the radial-direction magnetic field is canceled, so that the induced magnetic field from the built-in coil can be detected precisely.

Furthermore, in the first aspect, the at least one magnetic-field generating coil of the first magnetic-field generating unit may be an axial-direction magnetic-field generating coil that is disposed along a substantially cylindrical surface surrounding the detection space and that generates an axial-direction magnetic field in an axial direction of the substantially cylindrical surface.

Accordingly, even if the direction of the opening of the built-in coil in the detected object coincides with the axial direction of the detection space, by the operation of the axial-direction magnetic-field generating coil, it becomes possible to generate an induced magnetic field in the built-in coil and to thereby precisely detect the position of the detected object.

Furthermore, in the first aspect, the at least one magnetic-field generating coil of the second magnetic-field generating unit may be disposed along a substantially cylindrical surface surrounding the detection space and generate the second magnetic field in one radial direction of the substantially cylindrical surface.

Furthermore, in the first aspect, a switching unit may be provided that selects a magnetic-field generating coil to be operated according to at least one of position and orientation of the detected object from among the at least one magnetic-field generating coil provided in the first magnetic-field generating unit and the at least one magnetic-field generating coil provided in the second magnetic-field generating unit.

Furthermore, in the above configuration, the third magnetic-field generating unit may include at least one magnetic-field generating coil, and a switching unit may be provided that selects a magnetic-field generating coil to be operated according to at least one of position and orientation of the detected object from among the at least one magnetic-field generating coil provided in the first magnetic-field generating unit, the at least one magnetic-field generating coil provided in the second magnetic-field generating unit, and the at least one magnetic-field generating coil provided in the third magnetic-field generating unit.

Furthermore, in the first aspect, a control unit may be provided that controls an output of the first magnetic-field generating unit and an output of the second magnetic-field generating unit according to a value of mutual inductance between at least two magnetic-field generating coils among the at least one magnetic-field generating coil provided in the first magnetic-field generating unit and the at least one magnetic-field generating coil provided in the second magnetic-field generating unit.

Furthermore, in the above configuration, the third magnetic-field generating unit may include at least one magnetic-field generating coil, and a switching unit may be provided that selects a magnetic-field generating coil to be operated according to at least one of position and orientation of the detected object from among the at least one magnetic-field generating coil provided in the first magnetic-field generating unit, the at least one magnetic-field generating coil provided in the second magnetic-field generating unit, and the at least one magnetic-field generating coil provided in the third magnetic-field generating unit.

Furthermore, in the first aspect, a control unit may be provided that controls an output of the first magnetic-field generating unit and an output of the second magnetic-field generating unit according to a value of mutual inductance between at least two magnetic-field generating coils among the at least one magnetic-field generating coil provided in the first magnetic-field generating unit and the at least one magnetic-field generating coil provided in the second magnetic-field generating unit.

Furthermore, in the above configuration, the first magnetic-field generating unit and the second magnetic-field generating unit may be driven in synchronization with each other.

Alternatively, in the above configuration, the first magnetic-field generating unit and the third magnetic-field generating unit may be driven in synchronization with each other.

Furthermore, in the first aspect, the third magnetic-field generating unit may include at least one magnetic-field generating coil, and a control unit may be provided that controls an output of the first magnetic-field generating unit, an output of the second magnetic-field generating unit, and an output of the third magnetic-field generating unit according to a value of mutual inductance between at least two magnetic-field generating coils among the at least one magnetic-field generating coil provided in the first magnetic-field generating unit, the at least one magnetic-field generating coil provided in the second magnetic-field generating unit, and the at least one magnetic-field generating coil provided in the third magnetic-field generating unit.

Furthermore, in the first aspect, the at least one magnetic-field generating coil provided in the first magnetic-field generating unit and the at least one magnetic-field generating coil provided in the second magnetic-field generating unit may be connected to each other in series.

Alternatively, in the above configuration, the third magnetic-field generating unit may include at least one magnetic-field generating coil, and the at least one magnetic-field generating coil provided in the first magnetic-field generating unit and the at least one magnetic-field generating coil provided in the third magnetic-field generating unit may be connected to each other in series.

Accordingly, magnetic fields generated from two magnetic-field generating coils and having mutually opposite phases can be readily synchronized with each other.

Furthermore, a second aspect of the present invention is a medical device guiding system, wherein the detected object is a medical device provided with the circuit including the built-in coil and provided with a magnet, the medical device guiding system comprising any one of the position detecting devices described above and a fourth magnetic-field generating unit that includes at least one magnetic-field generating coil and that generates a fourth magnetic field applied to the magnet to guide the medical device.

According to the second aspect of the present invention, by applying the fourth magnetic field generated by the fourth magnetic-field generating unit to the magnet in the medical device, it is possible to move the medical device in the detection space. In this case, by using any one of the position detecting devices described above, precise position detection can be performed by the magnetic-field detecting unit, which is disposed in proximity to the medical device, so that the medical device can be guided precisely.

Furthermore, a third aspect of the present invention is a medical device guiding system, wherein the detected object is a medical device provided with the circuit including the built-in coil and provided with a magnet, the medical device guiding system comprising any one of the position detecting devices described above and a fourth magnetic-field generating unit that includes at least one magnetic-field generating coil and that generates a fourth magnetic field applied to the magnet to guide the medical device, wherein the position detecting device includes a control unit that controls an output of the first magnetic-field generating unit and an output of the second magnetic-field generating unit according to a value of mutual inductance between at least two magnetic-field generating coils among the at least one magnetic-field generating coil provided in the first magnetic-field generating unit, the at least one magnetic-field generating coil provided in the second magnetic-field generating unit, and the at least one magnetic-field generating unit provided in the fourth magnetic-field generating unit.

Furthermore, a fourth aspect of the present invention is a medical device guiding system, wherein the detected object is a medical device provided with the circuit including the built-in coil and provided with a magnet, the medical device guiding system comprising the position detecting device described above and a fourth magnetic-field generating unit that includes at least one magnetic-field generating coil and that generates a fourth magnetic field applied to the magnet to guide the medical device, wherein the third magnetic-field generating unit includes at least one magnetic-field generating coil, and the position detecting device includes a control unit that controls an output of the first magnetic-field generating unit and an output of the second magnetic-field generating unit according to a value of mutual inductance between at least two magnetic-field generating coils among the at least one magnetic-field generating coil provided in the first magnetic-field generating unit, the at least one magnetic-field generating coil provided in the second magnetic-field generating unit, the at least one magnetic-field generating coil provided in the third magnetic-field generating unit, and the at least one magnetic-field generating unit provided in the fourth magnetic-field generating unit.

Furthermore, a fifth aspect of the present invention is a position detecting method comprising a step of generating a first magnetic field in a detection space where a detected object provided with a circuit including at least one built-in coil is disposed; a step of detecting an induced magnetic field generated from the built-in coil by the generated first magnetic field; and a step of generating a second magnetic field including a magnetic-field component having a phase substantially opposite to the first magnetic field, wherein a generating direction of the first magnetic field and a detecting direction of the induced magnetic field intersect each other.

Furthermore, a sixth aspect of the present invention is a medical device guiding method, wherein the detected object is a medical device provided with the circuit including the built-in coil and a magnet, the medical device guiding method comprising the position detecting method described above and further comprising a step of generating a fourth magnetic field applied to the magnet to guide the medical device.

Furthermore, a seventh aspect of the present invention is a medical device guiding method, wherein the detected object is a medical device provided with the circuit including the built-in coil and a magnet, the medical device guiding method comprising the position detecting method described above and a step of generating a fourth magnetic field applied to the magnet to guide the medical device, wherein the position detecting method further includes a step of controlling an output of the first magnetic field and an output of the second magnetic field according to a value of mutual inductance between at least two magnetic fields among the generated first magnetic field, second magnetic field, and fourth magnetic field.

Furthermore, an eighth aspect of the present invention is a medical device guiding method, wherein the detected object is a medical device provided with the circuit including the built-in coil and a magnet, the medical device guiding method comprising the position detecting method described above and a step of generating a fourth magnetic field applied to the magnet to guide the medical device, wherein the position detecting method further includes a step of controlling an output of the first magnetic field and an output of the second magnetic field according to a value of mutual inductance between at least two magnetic fields among the generated first magnetic field, second magnetic field, third magnetic field, and fourth magnetic field.

An advantage is provided in that it is possible to dispose a magnetic-field detecting unit in proximity to a detected object, so that the position of the detected object can be detected precisely, while reducing the size and cost of the device.

Figure 1:
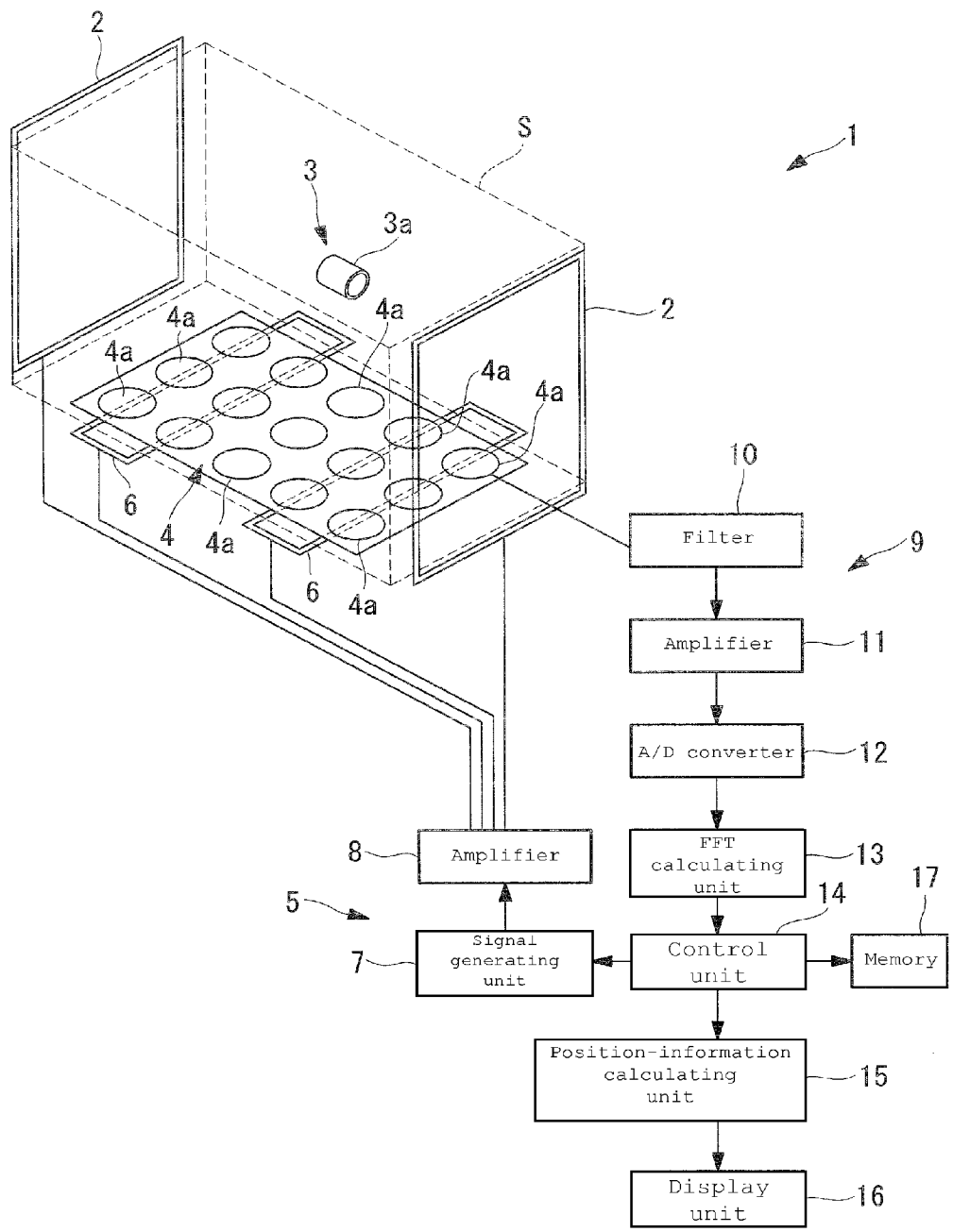
FIG. 1 is a schematic overall configuration diagram illustrating a position detecting device according to a first embodiment of the present invention.

EXPLANATION OF REFERENCE SIGNS $M_1$, $M_{11}$, $M_{12}$, $M_{13}$: First magnetic fields
$M_2$: Second magnetic fields
$M_{21}$: Opposite-phase magnetic fields (second magnetic fields)
$M_{22}$: Opposite-phase magnetic fields (third magnetic fields)
S: Detection space
1, 30: Position detecting devices
2: Magnetic-field generating coils (first magnetic field generating unit: first magnetic-field generating coils)
3: Detected object (medical device)
3a: Built-in coil
4: Magnetic-field sensor (magnetic-field detecting unit)
4a: Detecting coils
5: Driving unit
6, 33: Opposite-phase magnetic-field generating coils (second magnetic-field generating unit: second magnetic-field generating coils)
20: Medical device guiding system
21: Guiding-magnetic-field generating coil (fourth magnetic-field generating unit)
31a: Magnetic-field generating coils (first radial-direction magnetic-field generating coils)
31b: Magnetic-field generating coils (second radial-direction magnetic-field generating coils)

31c: Magnetic-field generating coils (axial-direction magnetic-field generating coils)

BEST MODE FOR CARRYING OUT THE INVENTION

A position detecting device 1 according to a first embodiment of the present invention will be described below with reference to FIGS. 1 to 5.

As shown in FIG. 1, the position detecting device 1 according to the first embodiment includes magnetic-field generating coils (first magnetic-field generating unit) 2 that generate an alternating magnetic field (hereinafter referred to as a first magnetic field $M_1$) penetrating a detection space S in one direction, a magnetic-field sensor (magnetic-field detecting unit) 4 that detects an induced magnetic field generated by a built-in coil 3a installed in a detected object 3, a driving unit 5 that drives and controls the magnetic-field generating coils 2, a detecting unit (magnetic-field detecting unit) 9 that processes signals output from a magnetic-field sensor 12, and opposite-phase-magnetic-field generating coils (second magnetic-field generating unit) 6 that generate opposite-phase magnetic fields (second magnetic fields $M_2$).

An example of the detected object 3 is a capsule medical device or the like that is introduced in the body of a subject or the like to perform a medical procedure.

The detected object 3, as shown in FIG. 1, is provided with an LC resonant circuit that is caused to resonate at a predetermined frequency and that is formed by a detected-piece closed circuit (not shown) including the built-in coil 3a and a capacitor (not shown) having a predetermined capacitance.

Although the LC resonant circuit may be used as a detected-piece closed circuit as described above, in a case where the predetermined resonant frequency can be achieved by a stray capacitance of the built-in coil 3a, a detected-piece closed circuit can be formed by the built-in coil 3a alone with both ends open.

Figure 2:
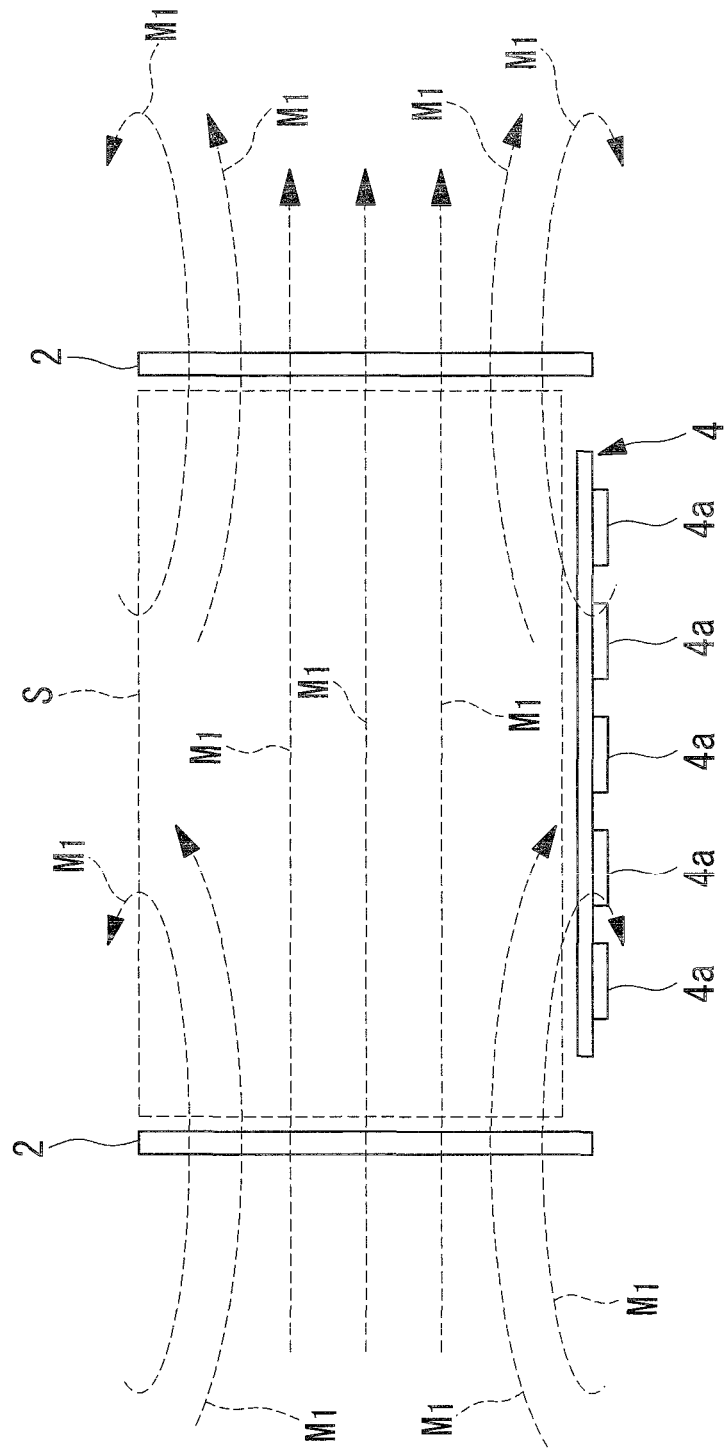
FIG. 2 is a side view schematically showing the placement of magnetic-field generating coils and a magnetic-field sensor in the position detecting device in FIG. 1 and a first magnetic field generated by the magnetic-field generating coils in a case where opposite-phase magnetic-field generating coils are not provided.

In the example shown in FIG. 1, for example, the magnetic-field generating coils 2 are wound in planar rectangle shapes, and are disposed at two positions so as to oppose each other on either side of the detection space. Thus, as shown in FIG. 2, the magnetic-field generating coils 2 are configured in the form of Helmholtz coils that generate a magnetic field in a direction along their opposing direction.

Furthermore, the magnetic-field generating coils 2 are electrically connected to the driving unit 5.

The driving unit 5 includes a signal generating unit 7 that outputs an AC signal having the frequency of the first magnetic field generated by the magnetic-field generating coils 2 and an amplifier 8 that amplifies the AC signal input from the signal generating unit 7 and drives the magnetic-field generating coils 2.

In the example shown in FIG. 1, the magnetic-field sensor 4 includes a plurality of (e.g., 15) detecting coils 4a that are arrayed two-dimensionally on a plane. The detecting coils 4a are disposed with the detecting direction thereof being in a direction perpendicular to the array plane thereof. Furthermore, the detecting coils 4a are electrically connected to the detecting unit 9.

Furthermore, the magnetic-field sensor 4 is disposed so that the detecting direction of the detecting coils 4a is perpendicular to the magnetic-field generating direction of the magnetic-field generating coils 2.

That is, as shown in FIG. 2, the magnetic-field sensor 4 is disposed on one face of the rectangular-block shaped detection space S, which is formed between the pair of magnetic-field generating coils 2 disposed opposing each other and substantially in parallel, with a gap therebetween.

The detecting unit 9 includes a filter 10 that cuts unwanted frequency components included in output signals (magnetic-field intensity signals) from the detecting coils 4a, an amplifier 11 that amplifies the output signals from which the unwanted components have been cut, an A/D converter 12 that converts the amplified output signals from analog signals to digital signals, and an FFT calculating unit 13 that performs an FFT calculation process on the basis of the output signals having been converted into the digital signals.

Furthermore, a control unit 14 is connected to the FFT calculating unit 13. Upon receiving a result of calculation by the FFT calculating unit 13, the control unit 14 sends the result of calculation to a position-information calculating unit 15 so that the position-information calculating unit 15 calculates the position of the built-in coil 3a, i.e., the position and orientation of the detected object 3, such as a capsule medical device. The calculated position and orientation of the detected object 3 are displayed on a display unit 16 and are stored in a memory 17.

Furthermore, the control unit 14 is configured to select an output signal of a certain detecting coil 4a from the output signals of the plurality of detecting coils 4a included in the magnetic-field sensor 4. Accordingly, it is possible to select only an output signal of a detecting coil 4a needed for position detection, so that the calculation load on the position-information calculating unit 15 can be reduced. As the output signal needed for position detection, an output signal having a strong signal intensity, an output signal from a detecting coil 4a located at a position a short distance from the detected object 3, or the like can be used.

The opposite-phase-magnetic-field generating coils 6 are coils formed in substantially planar shapes and are disposed at two positions individually opposing a plurality of detecting coils 4a (two sets of six detecting coils 4a in the example shown in FIG. 1) disposed in proximity to the two magnetic-field generating coils 2 among the detecting coils 4a constituting the magnetic-field sensor 4.

Each of the opposite-phase-magnetic-field generating coils 6 is configured to generate second magnetic fields $M_2$ along the detecting direction of the opposing detecting coils 4a.

Furthermore, in this embodiment, the two magnetic-field generating coils 2 and the two opposite-phase-magnetic-field generating coils 6 are connected to each other in series. Accordingly, it is possible to generate the first magnetic field $M_1$ and the second magnetic fields $M_2$ generated from the four magnetic-field generating coils 2 and 6 with the phases thereof completely synchronized.

The operation of the thus-configured position detecting device 1 according to this embodiment will be described below.

In order to detect, by using the position detecting device 1 according to this embodiment, the position of the detected object 3, such as a capsule medical device introduced in the body of a subject, first, in the driving unit 5, as shown in FIG. 1, the signal generating unit 7 generates an AC signal having a predetermined frequency. The generated AC signal is output to the amplifier 8. The amplifier 8 amplifies the input AC signal to a predetermined magnitude, and the amplified AC signal is output to the magnetic-field generating coils 2. Upon receiving the amplified AC signal, the magnetic-field generating coils 2 generate a first magnetic field in the vicinity thereof.

When the magnetic flux of the first magnetic field passes through the detected object 3, a resonant current having the predetermined frequency is induced in the detected-piece closed circuit including the built-in coil 3a installed inside the detected object 3. When the resonant current is induced in the detected-piece closed circuit, the resonant current causes the built-in coil 3a to form therearound an induced magnetic field having the predetermined frequency.

Since the magnetic flux associated with the first magnetic field and induced magnetic field described above passes through the detecting coils 4a of the magnetic-field sensor 4, the detecting coils 4a sense a combined magnetic field formed by adding these magnetic fields together and generate output signals that are induced currents based on changes in the magnetic flux passing therethrough. The output signals from the detecting coils 4a are output to the detecting unit 9.

In the detecting unit 9, the output signals that have been input are amplified by the amplifier 11, are converted into digital signals by the A/D converter 12, and are then subjected to FFT processing in the FFT calculating unit 13. Then, the result of the FFT processing is sent to the position-information calculating unit 15 via the control unit 14, where the position and orientation of the detected object 3 are calculated.

In this case, since the position detecting device 1 according to this embodiment includes the opposite-phase-magnetic-field generating coils 6, the position detecting device 1 has the following advantage.

That is, as shown in FIG. 2, in a case where the opposite-phase-magnetic-field generating coils 6 are not included, the magnetic-field generating coils 2 form the first magnetic field $M_1$ that is substantially linear in the proximity of the middle thereof, and form the first magnetic field $M_1$ that is curved so as to go round the wires of the magnetic-field generating coils 2 in the proximity of the periphery thereof.

In a case where it is possible to configure the magnetic-field generating coils 2 in a size sufficiently large relative to the detection space S, it is possible to form an ideal, linear first magnetic field $M_1$ in the entire region of the detection space S. In this case, however, the problem of increased size of the device arises.

In order to allocate a large detection space S and at the same time avoid an increase in the size of the device, it is necessary to dispose the detection space S also in the region where the first magnetic field $M_1$ generated by the magnetic-field generating coils 2 is curved, i.e., to dispose the magnetic-field sensor 4 in the region where the first magnetic field $M_1$ is curved. In this case, however, the curved magnetic field generated by the magnetic-field generating coils 2 directly passes through the detecting coils 4a of the magnetic-field sensor 4. Since the first magnetic field $M_1$ from the magnetic-field generating coils 2 is extremely large compared with the induced magnetic field generated from the built-in coil 3a in the detected object 3, the induced-magnetic-field signal from the built-in coil 3a becomes submerged in the magnetic-field signal from the magnetic-field generating coils 2.

Furthermore, in a case where, as in this embodiment, the generating direction of the first magnetic field $M_1$ by the magnetic-field generating coils 2 and the detecting direction of the induced magnetic field by the detecting coils 4a of the magnetic-field sensor 4 intersect each other, the direction of the first magnetic field $M_1$ entering the detecting coils 4a adjacent to one of the magnetic-field generating coils 2 differs from the direction of the first magnetic field $M_1$ entering the detecting coils 4a adjacent to the other magnetic-field detecting coil 2.

Figure 3:
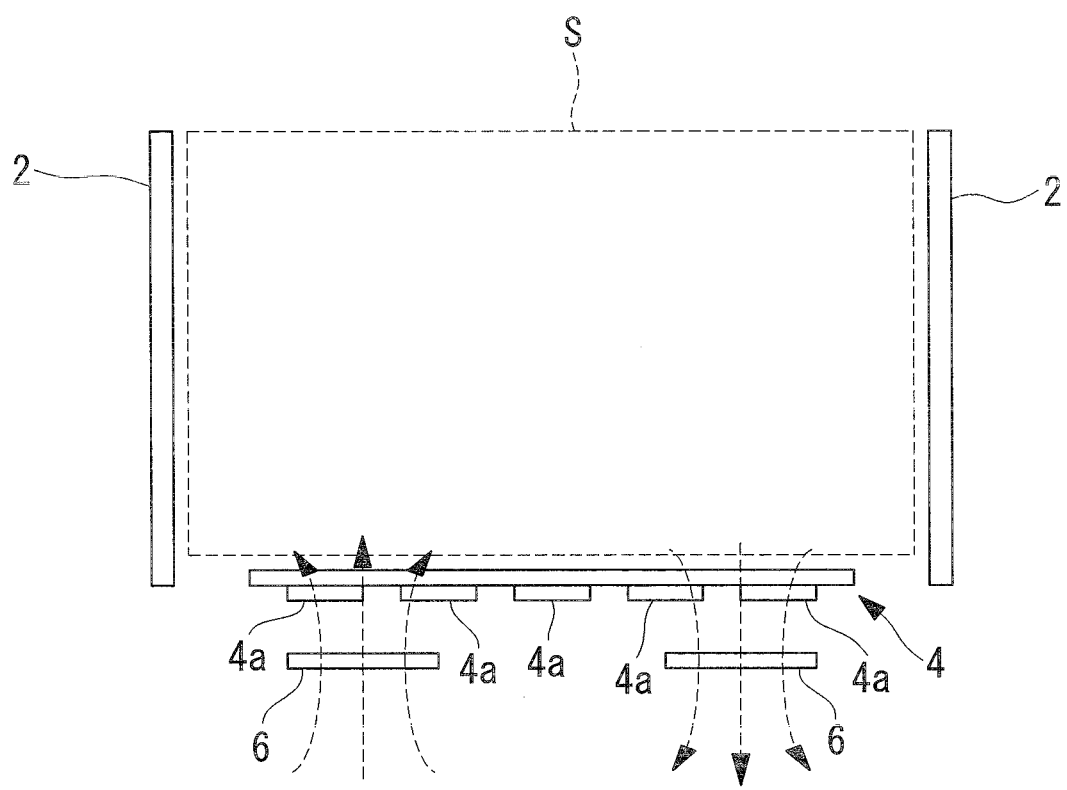
FIG. 3 is a side view schematically showing the placement of the magnetic-field generating coils and the magnetic-field sensor in the position detecting device in FIG. 1 and second magnetic fields generated by opposite-phase magnetic-field generating coils.

In the position detecting device 1 according to this embodiment, as shown in FIG. 3, the opposite-phase-magnetic-field generating coils 6 are disposed so as to individually oppose the detecting coils 4a into which the first magnetic field $M_1$ enters in different directions, so that second magnetic fields $M_2$ having magnetic-field components with phases opposite to the first magnetic field $M_1$ entering the detecting coils 4a are generated. Accordingly, the first magnetic field $M_1$ entering the detecting coils 4a is at least partially cancelled and weakened.

Figure 4:
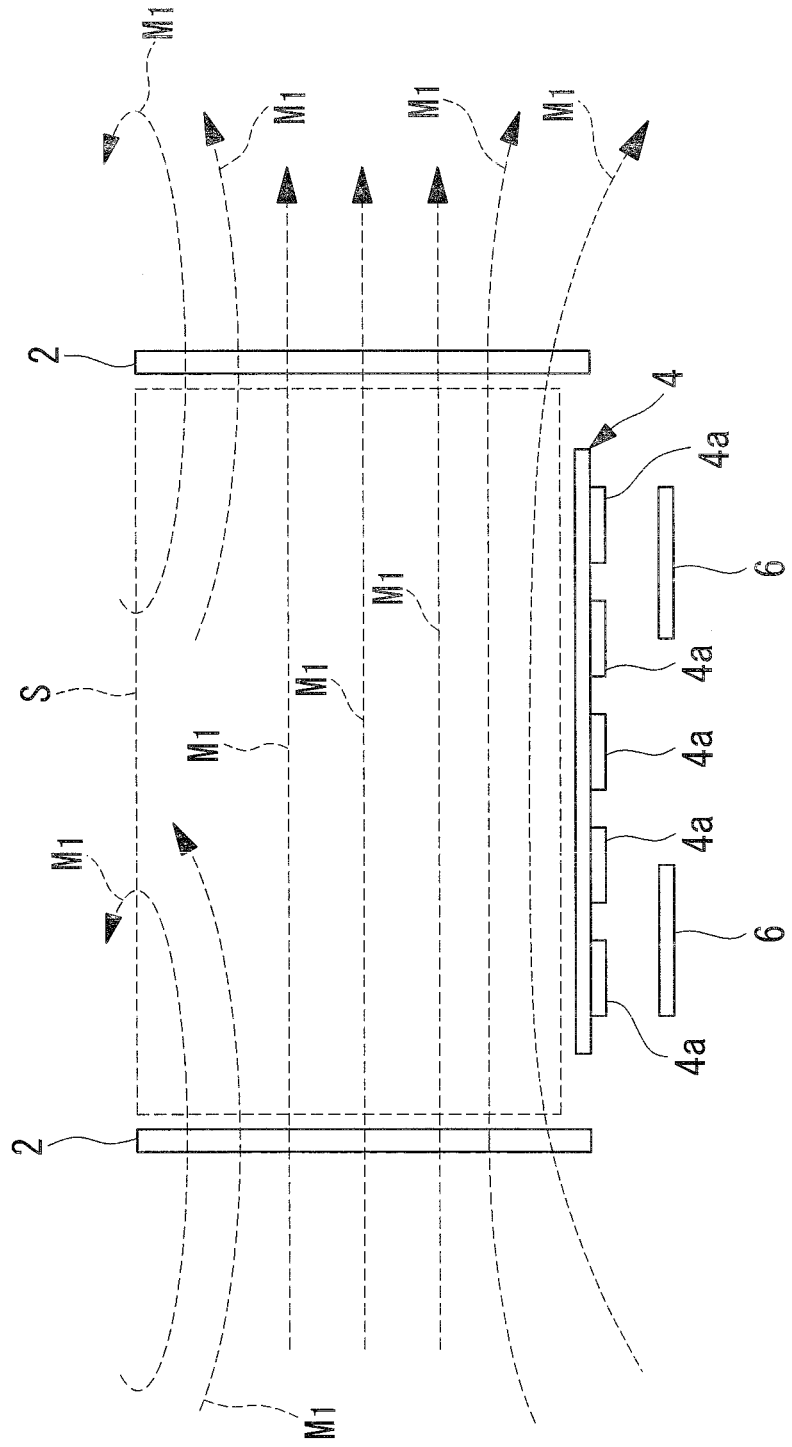
FIG. 4 is a side view schematically showing the placement of the magnetic-field generating coils and the magnetic-field sensor in the position detecting device in FIG. 1 and an ideal combined magnetic field in a case where opposite-phase magnetic-field generating coils are provided.
Figure 5:
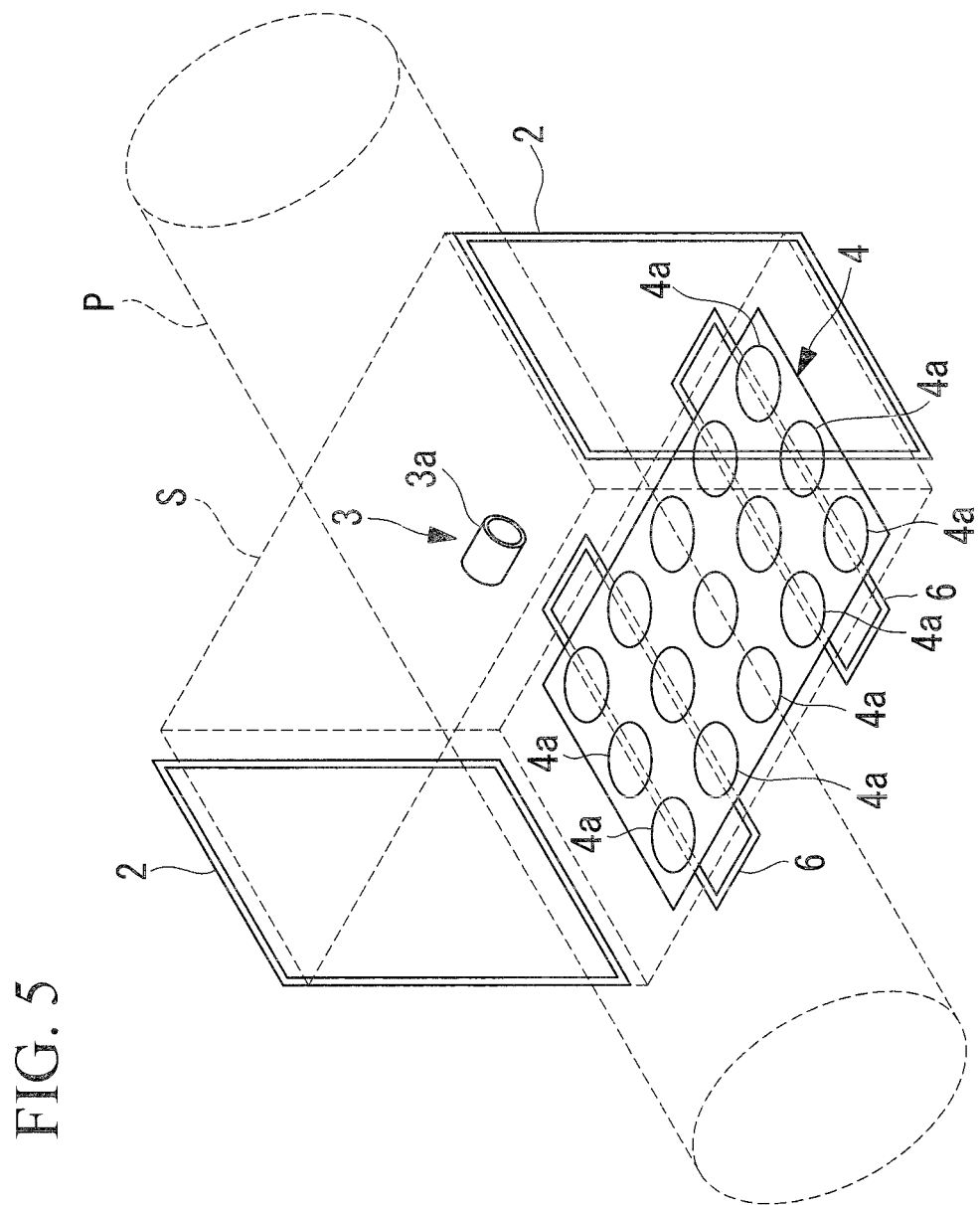
FIG. 5 is a perspective view illustrating an advantage of the position detecting device in FIG. 1.

Most ideally, as shown in FIG. 4, the first magnetic field $M_1$ entering the detecting coils 4a is fully cancelled, and the first magnetic field $M_1$ is formed linearly even in the proximity of the periphery of the magnetic-field generating coils 2.

As described above, in the position detecting device 1 according to this embodiment, although the detecting coils 4a are disposed so that the detecting direction thereof is perpendicular to the magnetic-field generating direction of the magnetic-field generating coils 2, the first magnetic field $M_1$ directly entering the detecting coils 4a from the magnetic-field generating coils 2 is suppressed or canceled out. This improves the SN ratio of induced-magnetic-field signals in signals detected by the detecting coils 4a, so that there is an advantage that the position of the detected object 3 can be detected precisely.

By making the magnetic-field generating direction of the magnetic-field generating coils 2 and the detecting direction of the magnetic-field sensor 4 perpendicular to each other as described above, as shown in FIG. 5, it is not necessary to dispose the magnetic-field sensor 4 so as to interfere with the magnetic-field generating direction, and it becomes possible to dispose an object P to be inspected through the magnetic-field generating coils 2. Furthermore, by making the magnetic-field generating direction of the magnetic-field generating coils 2 and the detecting direction of the magnetic-field sensor 4 perpendicular to each other as described above, as shown in FIG. 6, it becomes possible with the same single magnetic-field sensor 4 to detect induced magnetic fields based on first magnetic fields $M_{11}$ and $M_{12}$ generated in a plurality of different directions.

Figure 6:
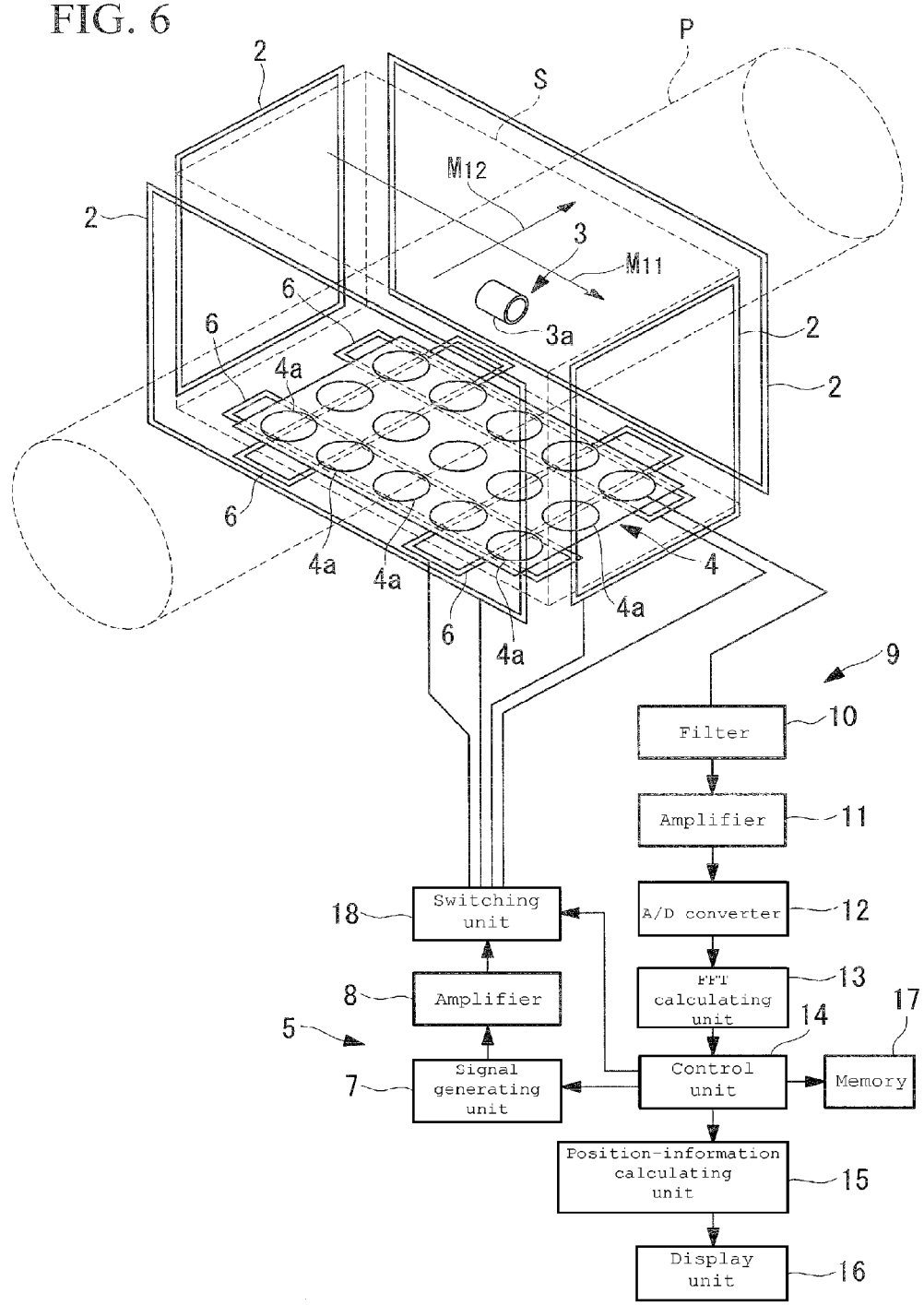
FIG. 6 is a perspective view illustrating a first modification of the position detecting device in FIG. 1.

In the example shown in FIG. 6, a switching unit 18 is provided, which selects a magnetic-field generating coil 2 and an opposite-phase-magnetic-field generating coil 6 to be operated according to at least one of the position and orientation of the built-in coil 3a, and the switching unit 18 is operated by an operation of the control unit 14.

Although this embodiment has been described regarding the example case where the magnetic-field generating coils 2 and the magnetic-field sensor 4 are perpendicular to each other, it is not limited to this example; the magnetic-field generating coils 2 and the magnetic-field sensor 4 may intersect each other at an angle other than 90°.

Furthermore, although Helmholtz coils having two opposing coils are given as an example of the magnetic-field generating coils 2, alternatively, the first magnetic field $M_1$ may be generated by a single magnetic-field generating coil 2.

Figure 7:
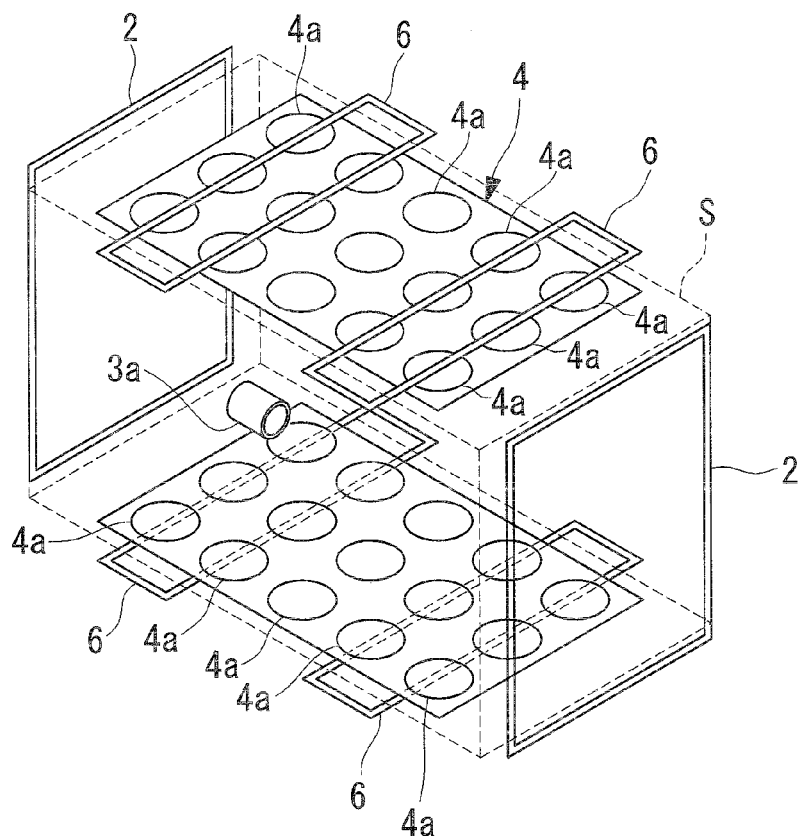
FIG. 7 is a perspective view illustrating a second modification of the position detecting device in FIG. 1.
Figure 8:
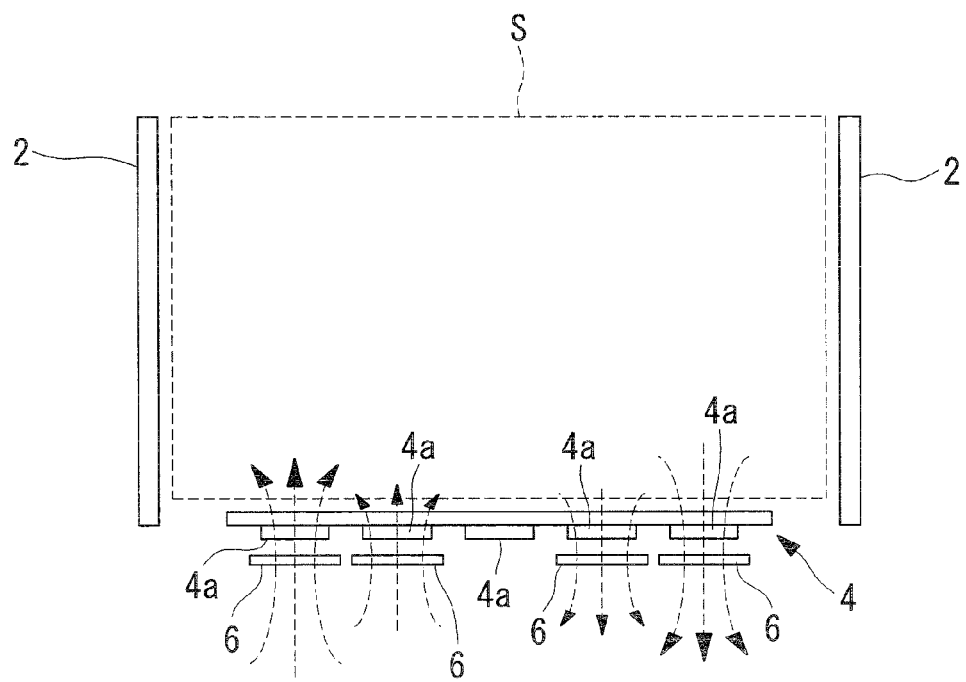
FIG. 8 is a side view illustrating a third modification of the position detecting device in FIG. 1.

Furthermore, although an induced magnetic field is detected by the single magnetic-field sensor 4 in this embodiment, alternatively, as shown in FIG. 7, two or more magnetic-field sensors 4 may be disposed. Also in this case, the detecting direction of the detecting coils 4a of each of the magnetic-field sensors 4 and the magnetic-field generating direction of the magnetic-field generating coils 2 intersect, and the opposite-phase-magnetic-field generating coils 6 are provided individually for the magnetic-field sensors 4. This serves to further improve the detection precision.

Furthermore, although the invention has been described above regarding the example case where each of the opposite-phase-magnetic-field generating coils 6 is disposed opposing a set of six detecting coils 4a, alternatively, as shown in FIG.

8, opposite-phase-magnetic-field generating coils 6 may be disposed individually opposing the detecting coils 4a, with the opposite-phase-magnetic-field generating coils 6 generating second magnetic fields $M_2$ having different intensities. Since the intensity of the first magnetic field $M_1$ entering the detecting coils 4a varies depending on the positions thereof relative to the magnetic-field generating coils 2, by providing the opposite-phase-magnetic-field generating coils 6 individually, the magnetic field $M_1$ entering the detecting coils 4a can be cancelled more effectively.

Figure 9:
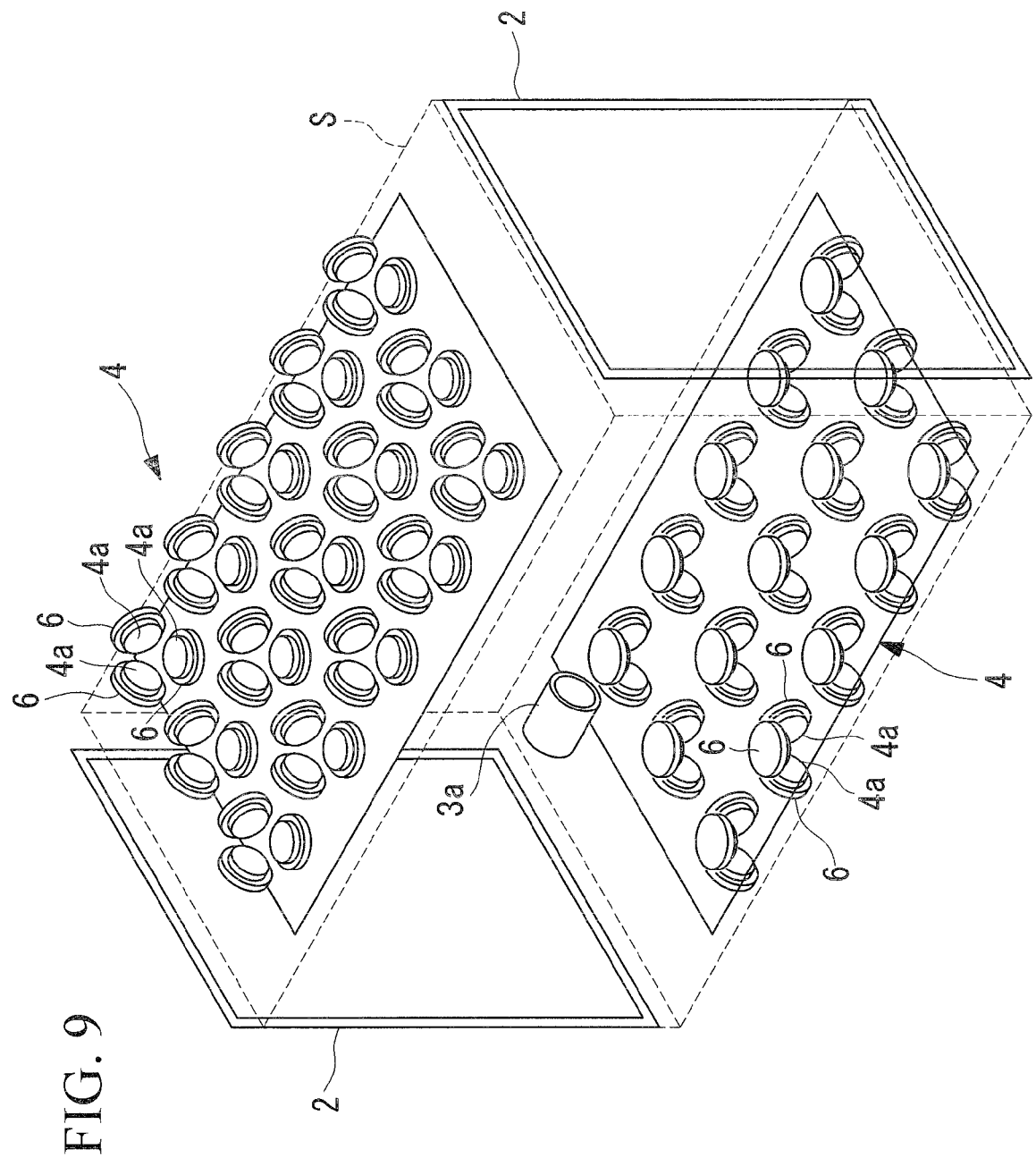
FIG. 9 is a perspective view illustrating a fourth modification of the position detecting device in FIG. 1.

Furthermore, in the case where the opposite-phase-magnetic-field generating coils 6 are provided individually for the detecting coils 4a, as shown in FIG. 9, a detecting coil 4a capable of detecting induced magnetic fields in three mutually perpendicular directions may be provided at each position.

Figure 10:
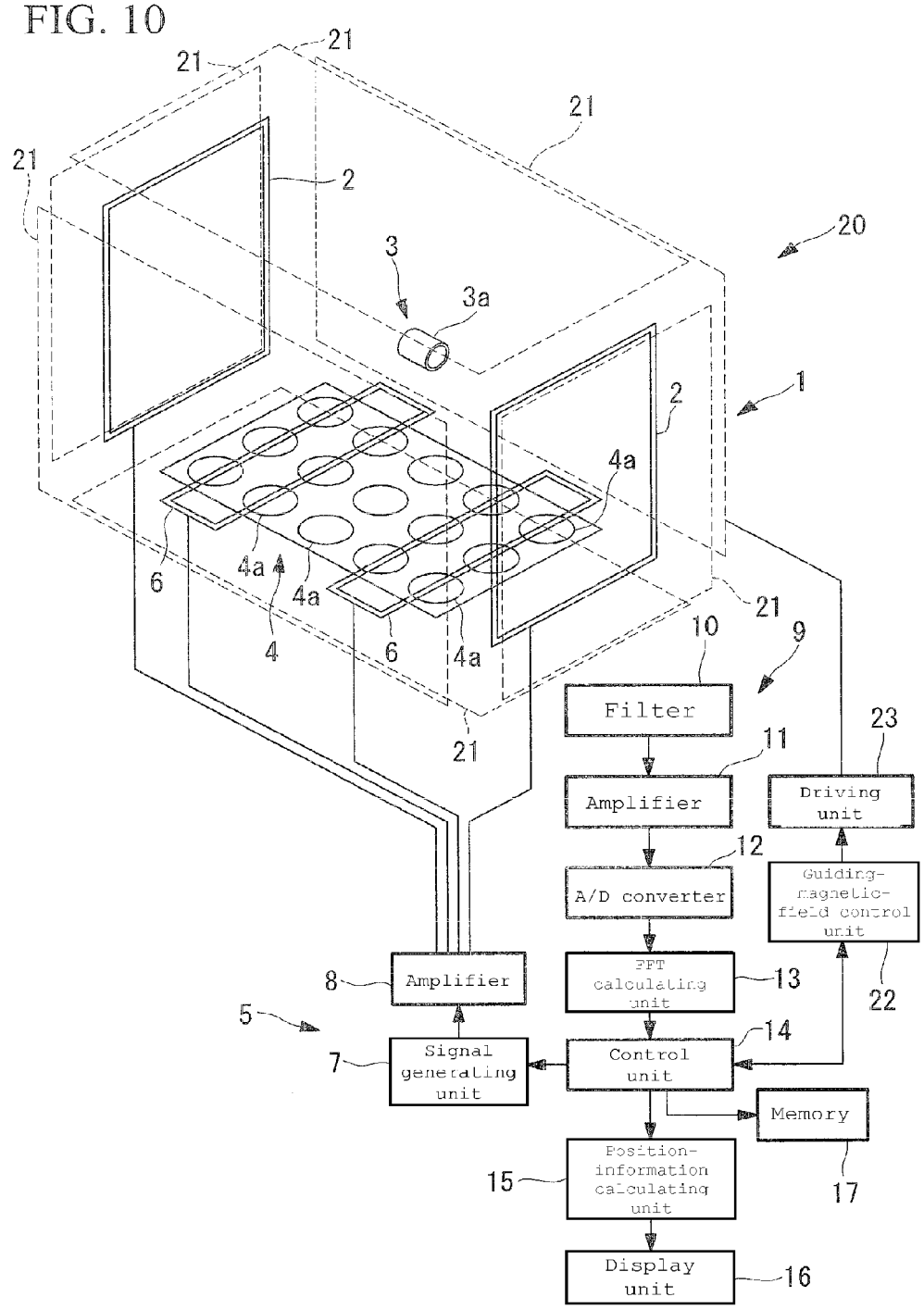
FIG. 10 is an overall configuration diagram schematically showing a medical device guiding system according to this embodiment, including the position detecting device in FIG. 1.

Furthermore, in a medical device guiding system 20 including the position detecting device 1 according to this embodiment, as shown in FIG. 10, in addition to the magnetic-field generating coils 2, guiding-magnetic-field generating coils 21 that generate guidance magnetic fields for guiding a medical device 3 are disposed. For example, a magnet (not shown) is disposed in the medical device 3, such as a capsule medical device or the distal end of an inserted portion of an endoscope, and the guiding-magnetic-field generating coils 21 are operated via a guiding-magnetic-field control unit 22 and a driving unit 23 according to an instruction from the control unit 14 so that the guidance magnetic fields act on the magnet from the outside. Accordingly, it is possible to generate a magnetic attracting force or a magnetic repelling force on the magnet so that the medical device 3 is guided in a desired direction.

In this case, when the magnetic-field generating coils 2 generate a first magnetic field $M_1$ for position detection of the medical device 3, by magnetic induction caused by the first magnetic field $M_1$ acting on the opposite-phase generating coils 6, interference magnetic fields are generated from the opposite-phase-magnetic-field generating coils 6 through electrical coupling, such as mutual inductance. Therefore, the intensities of second magnetic fields $M_2$ generated by the opposite-phase-magnetic-field generating coils 6 must be set in consideration of the interference magnetic fields generated by the opposite-phase generating coils 6 themselves, as well as the first magnetic field $M_1$ from the magnetic-field generating coils 2. Furthermore, since interference magnetic fields are also generated through electrical coupling between the magnetic-field generating coils 2 and opposite-phase-magnetic-field generating coils 6 and the guiding-magnetic-field generating coils 21, the intensities must be set in consideration of all the interference magnetic fields. Specifically, currents caused to flow through the individual coils, voltages applied to the individual coils, or outputs of the individual coils are controlled in consideration of the mutual inductances between the individual coils.

The sources of generation of interference magnetic fields are not limited to the guiding-magnetic-field generating coils 21, and other generating sources may exist, such as an electric-power generating coil provided inside the medical device 3, or a wireless-power-supply magnetic-field generating coil provided outside. Furthermore, the guiding-magnetic-field generating coils 21 may have core parts. In these cases, the intensities of the second magnetic fields $M_2$ from the opposite-phase-magnetic-field generating coils 6 must be adjusted in consideration of all these generating sources. The mutual inductances may be measured in advance to define the values thereof, or may be obtained by calculation when needed while measurement is taking place.

Furthermore, although the magnetic-field generating coils 2 and the opposite-phase-magnetic-field generating coils 6 are connected in series in the position detecting device 1 according to this embodiment in order to simply and reliably synchronize the first magnetic field $M_1$ and the second magnetic fields $M_2$ that are generated, alternatively, a parallel connection may be used so that the first magnetic field $M_1$ and the second magnetic fields $M_2$ are synchronized by other means.

Next, a position detecting device 30 according to a second embodiment of the present invention will be described below with reference to FIGS. 11 to 15.

In the description of this embodiment, parts configured identically to those of the position detecting device 1 according to the first embodiment are designated by the same reference signs, and a description thereof will be omitted.

Figure 11:
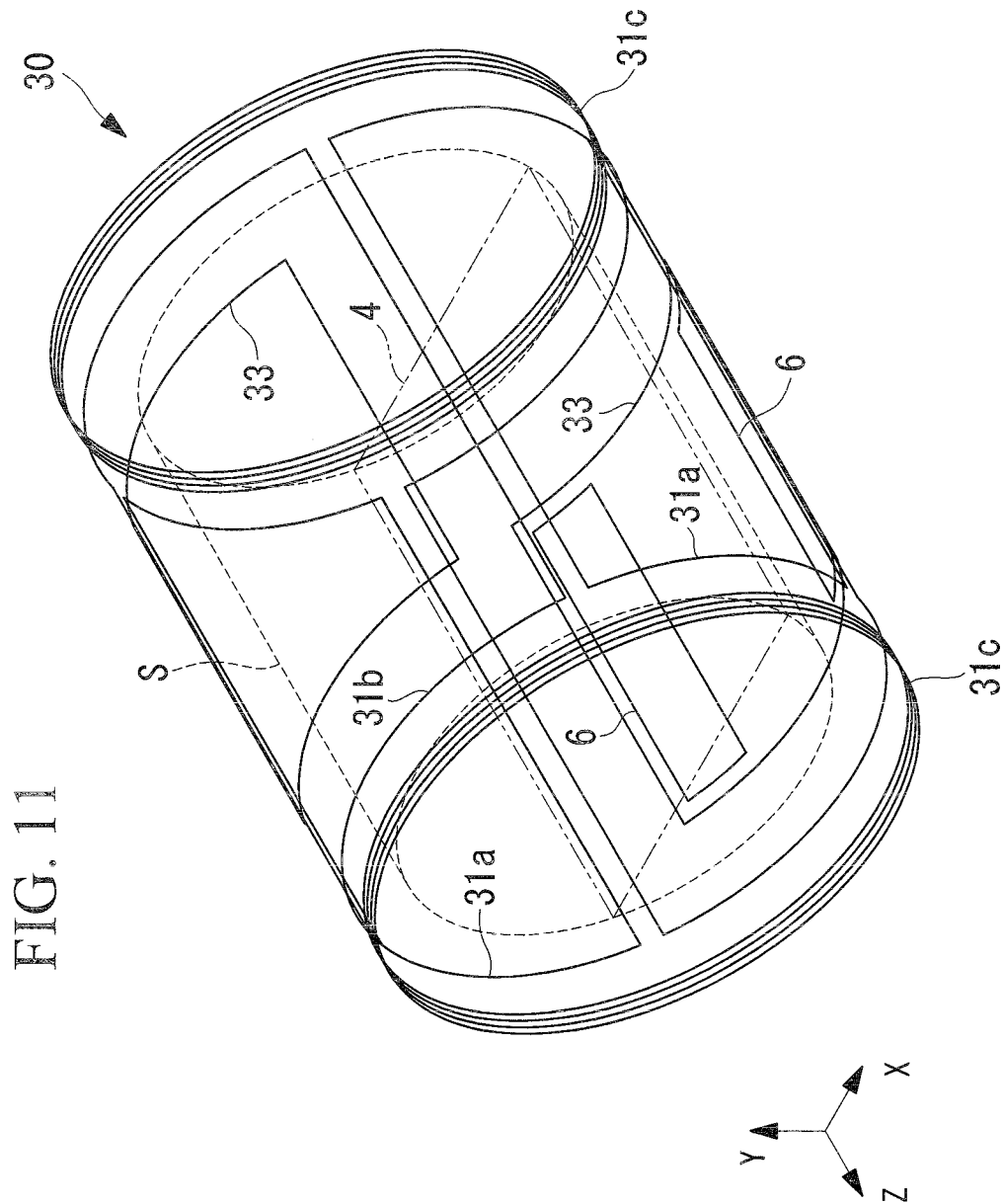
FIG. 11 is a perspective view showing a position detecting device according to a second embodiment of the present invention.

The position detecting device 30 according to this embodiment differs from the position detecting device 1 according to the first embodiment in that, as shown in FIG. 11, magnetic-field generating coils 6, 31a to 31c, and 33 are disposed along a cylindrical surface.

As shown in FIG. 11, the position detecting device 30 according to this embodiment includes magnetic-field generating coils 31a that are disposed at positions on either side of a detection space S in a radial direction, the detection space S having a center line in a substantially horizontal direction, and that generate a substantially horizontal first magnetic field $M_{11}$ along an X direction; magnetic-field generating coils 31b that are disposed on either side of the detection space S in a radial direction and that generate a substantially vertical first magnetic field $M_{12}$ along a Y direction; and magnetic-field generating coils 31c that are disposed on either side of the detection space S in an axial direction and that generate a first magnetic field $M_{13}$ along the axial direction (Z direction).

Figure 12:
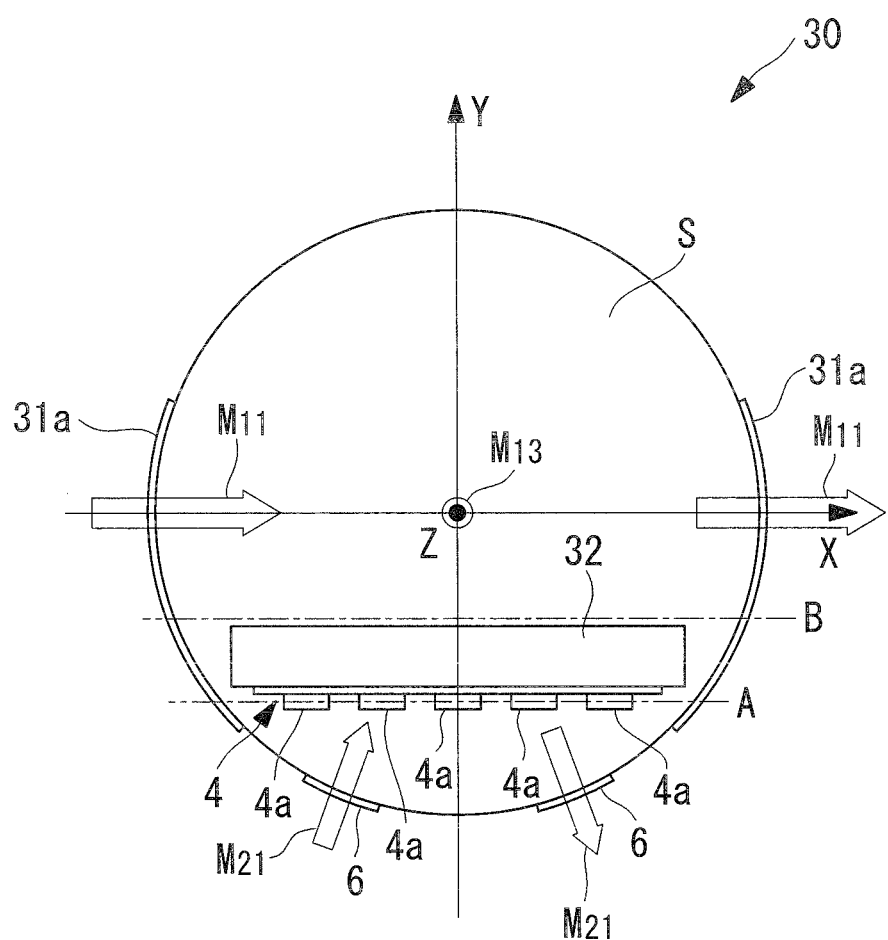
FIG. 12 is a front view illustrating the placement of magnetic-field generating coils that generate a first magnetic field along an X direction, a magnetic-field sensor, and opposite-phase magnetic-field generating coils in the position detecting device in FIG. 11.
Figure 13:
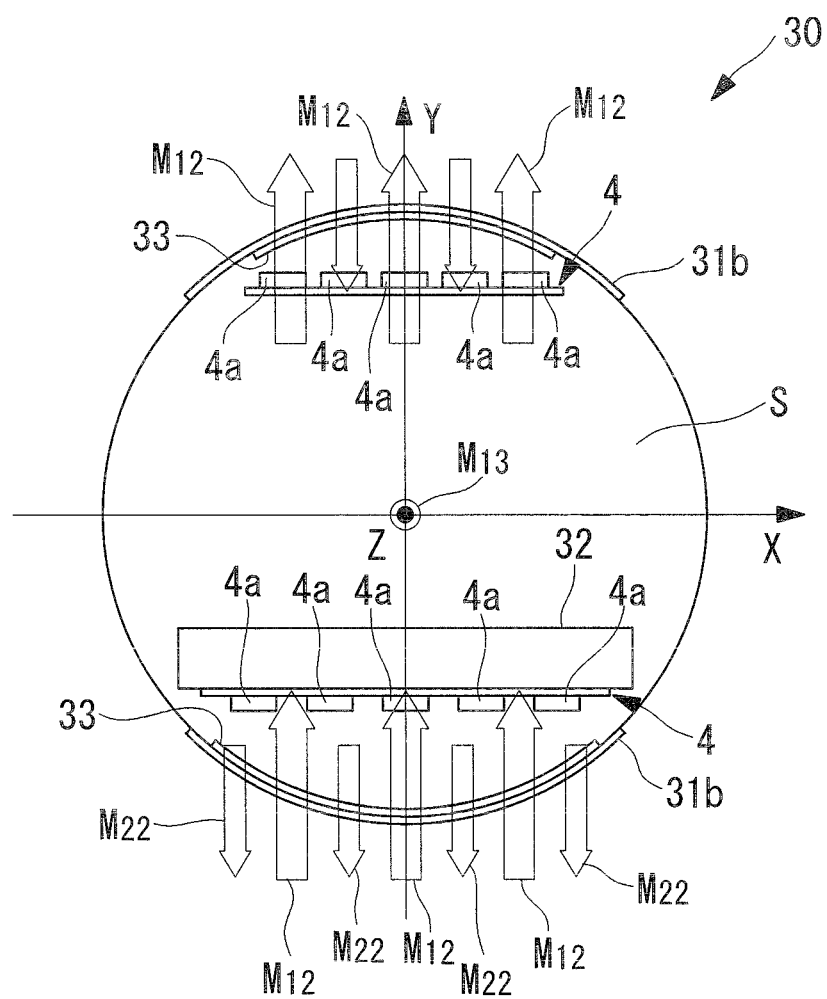
FIG. 13 is a front view illustrating the placement of magnetic-field generating coils that generate a first magnetic field along a Y direction, a magnetic-field sensor, and opposite-phase magnetic-field generating coils in the position detecting device in FIG. 11.

Furthermore, in the detection space S, as shown in FIGS. 12 and 13, a substantially horizontal bed 32 is disposed along the axial direction so that a subject, which is an object to be inspected, can be disposed lying horizontally.

For simplicity of description, FIG. 12 shows the placement of the magnetic-field generating coils 31a that generate the first magnetic field $M_{11}$ and the opposite-phase-magnetic-field generating coils 6 associated therewith.

Furthermore, FIG. 13 shows the placement of the magnetic-field generating coils 31b that generate the first magnetic field $M_{12}$ and the opposite-phase-magnetic-field generating coils 33 associated therewith.

The magnetic-field sensors 4 are disposed under the bed 32 and over the bed. In FIG. 12, the upper magnetic sensor 4 is not shown since it is disposed at a position where second magnetic fields $M_{21}$ having phases opposite to the first magnetic field $M_{11}$ is not necessary.

Furthermore, below the magnetic sensor 4, as shown in FIG. 12, the opposite-phase-magnetic-field generating coils 6 are provided at two positions, which generate second magnetic fields $M_{21}$ having phases opposite to the first magnetic field $M_{11}$ generated by the magnetic-field generating coils 31a for partial sets of detecting coils 4a in groups of the plurality of detecting coils 4a included in the magnetic-field sensor 4.

Figures 14, 15:
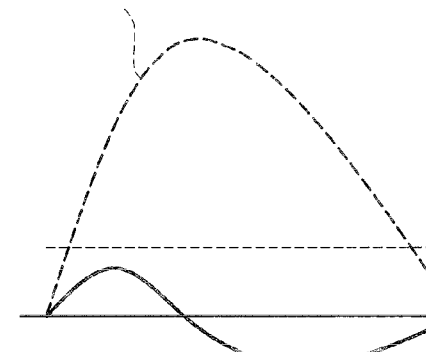
FIG. 14 is a graph showing a distribution of magnetic-field intensity in the Y direction along a chain line A in FIG. 12.
FIG. 15 is a graph showing a distribution of magnetic-field intensity in the Y direction along a chain line B in FIG. 12.

FIGS. 14 and 15 respectively show the magnetic-field intensity in the Y direction along a chain line A and the magnetic-field intensity in the Y direction along a chain line B in FIG. 12. According to FIG. 14, it is understood that in a case where the opposite-phase-magnetic-field generating coils 6 are absent (in the case of the graph indicated by a broken line), a combined magnetic field exceeding the detecting range of the detecting coils 4a (sensor detecting range) enters the detecting coils 4a. On the other hand, in a case where the opposite-phase-magnetic-field generating coils 6 are operated (in the case of the graph indicated by a solid line), a combined magnetic field that enters the detecting coils 4a is suppressed, so that the magnetic-field intensity of the combined magnetic field can be suppressed within the detecting range of the detecting coils 4a.

Furthermore, according to FIG. 15, it is understood that the distribution of magnetic-field intensity in the X direction over the bed 32 is maintained substantially uniform regardless of the presence or absence of the opposite-phase-magnetic-field generating coils 6. As a result, it is possible to weaken the intensity of the combined magnetic field that enters the detecting coils 4a while maintaining the magnetic-field intensity in the detection space S. That is, there is an advantage that a magnetic field having an intensity needed for the detection space S can be generated without degrading the detection precision.

Furthermore, as shown in FIG. 13, further below the lower magnetic sensor 4, a magnetic-field generating coil 31b that generates a first magnetic field $M_{12}$ along the Y direction and an opposite-phase-magnetic-field generating coil 33 that generates an opposite-phase magnetic field $M_{22}$ (third magnetic field) for canceling the first magnetic field $M_{12}$ in the proximity of the detecting coils 4a of the magnetic-field sensor 4 are disposed. Furthermore, further above the upper magnetic-field sensor 4, a magnetic-field generating coil 31b that generates a first magnetic field $M_{12}$ along the Y direction and an opposite-phase-magnetic-field generating coil 33 that generates an opposite-phase magnetic field $M_{22}$ (third magnetic field) for canceling the first magnetic field $M_{12}$ in the proximity of the detecting coils 4a are disposed.

Since the first magnetic fields $M_{12}$ are generated in the Y direction, which is the detecting direction of the detecting coils 4a constituting the magnetic-field sensors 4, the first magnetic fields $M_{12}$ operate equally on all the detecting coils 4a. Therefore, a single opposite-phase-magnetic-field generating coil 33 is disposed for each of the magnetic-field sensors 4 so that the opposite-phase magnetic fields $M_{22}$ for canceling the first magnetic fields $M_{12}$ also operate equally on all the detecting coils 4a.

These magnetic-field generating coils 31a and 31b and opposite-phase-magnetic-field generating coils 6 and 33 are both provided so as to surround the detection space S along cylindrical surfaces having substantially the same diameter.

Furthermore, the magnetic-field generating coils 31c that generate a first magnetic field $M_{13}$ along the Z direction are formed by substantially circular coils disposed on either side the detection space in the axial direction. Since the magnetic-field generating coils 31c are formed as Helmholtz coils that are large relative to the detecting space S in order to meet the need of placing a subject through the openings thereof, the first magnetic field $M_{13}$ is formed substantially linearly in the axial direction. Therefore, it is not necessary to provide opposite-phase-magnetic-field generating coils for the first magnetic field $M_{13}$.

Furthermore, the detection space S is not limited to a substantially cylindrical shape, and may be formed in a substantially rectangular block shape.

As described above, in the position detecting device 30 according to this embodiment, the magnetic-field generating coils 31a to 31c are disposed along cylindrical surfaces surrounding the detection space S, and the magnetic-field sensor 4 is provided in proximity to and under the bed 32 disposed in the detection space S. Therefore, the detection space S is not interfered with by the magnetic-field sensor 4, so that the entire device can be configured in a compact form while allocating a large space for accommodating an object to be detected, such as a subject.

As a result, it is possible to dispose the magnetic-field sensor 4 at a position near the detected object 3 and to use coils having a relatively low sensitivity as the detecting coils 3a. Furthermore, the detection space S can be reduced to a minimum necessary size, so that electric power supplied to the magnetic-field generating coils 31a, 31b, and 31c can be reduced.

Furthermore, by forming the first magnetic field $M_{11}$ along the X direction, the first magnetic field $M_{12}$ along the Y direction, and the first magnetic field $M_{13}$ along the Z direction in the detection space S and performing switching among $M_{11}$, $M_{12}$, and $M_{13}$ according to the position of the detected object 3, the detected object 3 disposed in the detection space S is not lost from detection regardless of the orientation of the detected object 3, so that the position and orientation thereof can be detected precisely.

The invention claimed is:

1. A position detecting device comprising:
a first magnetic-field generating unit that includes at least one magnetic-field generating coil and that generates a first magnetic field in a detection space where a detected object provided with a circuit including at least one built-in coil is disposed;
a magnetic-field detecting unit that includes a plurality of detecting coils arrayed to detect an induced magnetic field generated from the built-in coil by the first magnetic field generated by the first magnetic-field generating unit; and
a second magnetic-field generating unit that includes at least one magnetic-field generating coil and that generates a second magnetic field, which includes a magnetic-field component having a phase substantially opposite to the first magnetic field generated by the first magnetic-field generating unit and entering the detecting coils,
wherein the first magnetic-field generating unit and the detecting coils are disposed so that a generating direction, normal to the cross-section of the at least one magnetic-field generating coil of the first magnetic-field generating unit, and a detecting direction, normal to the cross-section of the detecting coils, intersect each other,
wherein the second magnetic-field generating unit is disposed at a location where at least one of the plurality of detecting coils disposed adjacent to the first magnetic-field generating unit is disposed; and
wherein the second magnetic-field generating unit is not disposed at a location where at least one of the plurality of detecting coils disposed apart from the first magnetic-field generating unit in comparison to the at least one of the plurality of detecting coils disposed adjacent to the first magnetic-field generating unit is disposed.

2. A position detecting device according to claim 1, wherein the first magnetic-field generating unit and the detecting coils are disposed so that the generating direction, normal to the cross-section of the at least one magnetic-field generating coil of the first magnetic-field generating unit, and the detecting direction, normal to the cross-section of the detecting coils, intersect each other substantially perpendicularly.

3. A position detecting device according to claim 1, wherein the second magnetic-field generating unit generates second magnetic fields having different intensities according to positions of the individual detecting coils relative to the first magnetic-field generating unit.

4. A position detecting device according to claim 3, wherein the second magnetic-field generating unit generates second magnetic fields having different intensities for a plurality of sets of detecting coils that are grouped on the basis of their positions relative to the first magnetic-field generating unit.

5. A position detecting device according to claim 3, wherein the second magnetic-field generating unit is provided individually for each of the detecting coils.

6. A position detecting device according to claim 1, wherein the at least one magnetic-field generating coil of the first magnetic-field generating unit is a radial-direction magnetic-field generating coil that is disposed along a substantially cylindrical surface surrounding the detection space and that generates the first magnetic field in one radial direction of the substantially cylindrical surface.

7. A position detecting device according to claim 1, wherein the at least one magnetic-field generating coil of the first magnetic-field generating unit is a first radial-direction magnetic-field generating coil that is disposed along a substantially cylindrical surface surrounding the detection space and that generates the first magnetic field in one radial direction of the substantially cylindrical surface and a second radial-direction magnetic-field generating coil that is disposed along the substantially cylindrical surface and that generates a radial-direction magnetic field in a radial direction of the substantially cylindrical surface, the radial direction intersecting the first magnetic field generated by the first radial-direction magnetic-field generating coil.

8. A position detecting device according to claim 7, wherein
the generating direction of the radial-direction magnetic field generated by the second radial-direction magnetic-field generating coil coincides with the detecting direction of the induced magnetic field by the detecting coils, and
the position detecting device comprises a third magnetic-field generating unit that generates a third magnetic field having a phase substantially opposite to the radial-direction magnetic field generated by the second radial-direction magnetic-field generating coil and entering any of the detecting coils.

9. A position detecting device according to claim 8, wherein
the third magnetic-field generating unit includes at least one magnetic-field generating coil, and
the position detecting device comprises a switching unit that selects a magnetic-field generating coil to be operated according to at least one of position and orientation of the detected object from among the at least one magnetic-field generating coil provided in the first magnetic-field generating unit, the at least one magnetic-field generating coil provided in the second magnetic-field generating unit, and the at least one magnetic-field generating coil provided in the third magnetic-field generating unit.

10. A position detecting device according to claim 9, comprising a control unit that controls an output of the first magnetic-field generating unit, an output of the second magnetic-field generating unit, and an output of the third magnetic-field generating unit according to a value of mutual inductance between at least two magnetic-field generating coils among the at least one magnetic-field generating coil provided in the first magnetic-field generating unit, the at least one magnetic-field generating coil provided in the second magnetic-field generating unit, and the at least one magnetic-field generating coil provided in the third magnetic-field generating unit.

11. A position detecting device according to claim 9, wherein the at least one magnetic-field generating coil provided in the first magnetic-field generating unit and the at least one magnetic-field generating coil provided in the third magnetic-field generating unit are connected to each other in series.

12. A position detecting device according to claim 8, wherein
the third magnetic-field generating unit includes at least one magnetic-field generating coil, and
the position detecting device comprises a control unit that controls an output of the first magnetic-field generating unit, an output of the second magnetic-field generating unit, and an output of the third magnetic-field generating unit according to a value of mutual inductance between at least two magnetic-field generating coils among the at least one magnetic-field generating coil provided in the first magnetic-field generating unit, the at least one magnetic-field generating coil provided in the second magnetic-field generating unit, and the at least one magnetic-field generating coil provided in the third magnetic-field generating unit.

13. A position detecting device according to claim 8, wherein the first magnetic-field generating unit and the third magnetic-field generating unit are driven in synchronization with each other.

14. A position detecting device according to claim 8, wherein
the third magnetic-field generating unit includes at least one magnetic-field generating coil, and
the at least one magnetic-field generating coil provided in the first magnetic-field generating unit and the at least one magnetic-field generating coil provided in the third magnetic-field generating unit are connected to each other in series.

15. A medical device guiding system comprising:
a position detecting device according to claim 8,
wherein the detected object is a medical device provided with the circuit including the built-in coil and provided with a magnet,
the medical device guiding system further comprising a fourth magnetic-field generating unit that includes at least one magnetic-field generating coil and that generates a fourth magnetic field applied to the magnet to guide the medical device.

16. A medical device guiding system comprising:
a position detecting device according to claim 8,
wherein the detected object is a medical device provided with the circuit including the built-in coil and provided with a magnet,
the medical device guiding system further comprising a fourth magnetic-field generating unit that includes at least one magnetic-field generating coil and that generates a fourth magnetic field applied to the magnet to guide the medical device,
wherein the position detecting device includes a control unit that controls an output of the first magnetic-field generating unit and an output of the second magnetic-field generating unit according to a value of mutual inductance between at least two magnetic-field generating coils among the at least one magnetic-field generating coil provided in the first magnetic-field generating unit, the at least one magnetic-field generating coil provided in the second magnetic-field generating unit, and the at least one magnetic-field generating coil provided in the fourth magnetic-field generating unit.

17. A medical device guiding system comprising:
a position detecting device according to claim 8,
wherein the detected object is a medical device provided with the circuit including the built-in coil and provided with a magnet,
the medical device guiding system further comprising a fourth magnetic-field generating unit that includes at least one magnetic-field generating coil and that generates a fourth magnetic field applied to the magnet to guide the medical device,
wherein the third magnetic-field generating unit includes at least one magnetic-field generating coil, and the position detecting device includes a control unit that controls an output of the first magnetic-field generating unit and an output of the second magnetic-field generating unit according to a value of mutual inductance between at least two magnetic-field generating coils among the at least one magnetic-field generating coil provided in the first magnetic-field generating unit, the at least one magnetic-field generating coil provided in the second magnetic-field generating unit, the at least one magnetic-field generating coil provided in the third magnetic-field generating unit, and the at least one magnetic-field generating coil provided in the fourth magnetic-field generating unit.

18. A position detecting device according to claim 1, wherein the at least one magnetic-field generating coil of the first magnetic-field generating unit is an axial-direction magnetic-field generating coil that is disposed along a substantially cylindrical surface surrounding the detection space and that generates an axial-direction magnetic field in an axial direction of the substantially cylindrical surface.

19. A position detecting device according to claim 1, wherein the at least one magnetic-field generating coil of the second magnetic-field generating unit is disposed along a substantially cylindrical surface surrounding the detection space and generates the second magnetic field in one radial direction of the substantially cylindrical surface.

20. A position detecting device according to claim 1, comprising a switching unit that selects a magnetic-field generating coil to be operated according to at least one of position and orientation of the detected object from among the at least one magnetic-field generating coil provided in the first magnetic-field generating unit and the at least one magnetic-field generating coil provided in the second magnetic-field generating unit.

21. A position detecting device according to claim 1, comprising a control unit that controls an output of the first magnetic-field generating unit and an output of the second magnetic-field generating unit according to a value of mutual inductance between at least two magnetic-field generating coils among the at least one magnetic-field generating coil provided in the first magnetic-field generating unit and the at least one magnetic-field generating coil provided in the second magnetic-field generating unit.

22. A position detecting device according to claim 1, wherein the first magnetic-field generating unit and the second magnetic-field generating unit are driven in synchronization with each other.

23. A position detecting device according to claim 1, wherein the at least one magnetic-field generating coil provided in the first magnetic-field generating unit and the at least one magnetic-field generating coil provided in the second magnetic-field generating unit are connected to each other in series.

24. A position detecting method comprising:
a step of generating, by a first magnetic-field generating unit, a first magnetic field in a detection space where a detected object provided with a circuit including at least one built-in coil is disposed;
a step of detecting, by a plurality of detecting coils, an induced magnetic field generated from the built-in coil by the generated first magnetic field; and
a step of generating, by a second magnetic-field generating unit, a second magnetic field including a magnetic-field component having a phase substantially opposite to the first magnetic field,
wherein a generating direction of the first magnetic field and a detecting direction of the induced magnetic field intersect each other,
wherein the second magnetic-field generating unit is disposed at a location where at least one of the plurality of detecting coils disposed adjacent to the first magnetic-field generating unit is disposed; and
wherein the second magnetic-field generating unit is not disposed at a location where at least one of the plurality of detecting coils disposed apart from the first magnetic-field generating unit in comparison to the at least one of the plurality of detecting coils disposed adjacent to the first magnetic-field generating unit is disposed.

25. A position detecting method according to claim 24, wherein the generating direction of the first magnetic field and the detecting direction of the induced magnetic field intersect each other substantially perpendicularly.

26. A position detecting method according to claim 24, wherein second magnetic fields having different intensities are generated according to the generated first magnetic field.

27. A position detecting method according to claim 26, wherein second magnetic fields having different intensities are generated for groups defined according to the generated first magnetic field.

28. A position detecting method according to claim 24, wherein the first magnetic field is generated in one radial direction of a substantially cylindrical surface surrounding the detection space.

29. A position detecting method according to claim 24, wherein a radial-direction magnetic field is generated in a radial direction of a substantially cylindrical surface, the radial direction intersecting the generated first magnetic field.

30. A position detecting method according to claim 29, wherein
the generating direction of the radial-direction magnetic field coincides with the detecting direction of the induced magnetic field, and
a third magnetic field having a phase substantially opposite to the radial-direction magnetic field is generated.

31. A position detecting method according to claim 30, further comprising a step of selecting a magnetic field to be generated from among the first magnetic field, the second magnetic field, and the third magnetic field according to at least one of position and orientation of the detected object.

32. A position detecting method according to claim 31, further comprising a step of controlling an output of the first magnetic field, an output of the second magnetic field, and an output of the third magnetic field according to a value of mutual inductance between at least two magnetic fields among the generated first magnetic field, second magnetic field, and third magnetic field.

33. A position detecting method according to claim 30, further comprising a step of controlling an output of the first magnetic field, an output of the second magnetic field, and an output of the third magnetic field according to a value of mutual inductance between at least two magnetic fields among the generated first magnetic field, second magnetic field, and third magnetic field.

34. A position detecting method according to claim 30, wherein the first magnetic field and the third magnetic field are synchronized with each other.

35. A medical device guiding method comprising:
a position detecting method according to claim 30,
wherein the detected object is a medical device provided with the circuit including the built-in coil and a magnet,
the medical device guiding method further comprising a step of generating a fourth magnetic field applied to the magnet to guide the medical device.

36. A medical device guiding method comprising:
a position detecting method according to claim 30,
wherein the detected object is a medical device provided with the circuit including the built-in coil and a magnet,
the medical device guiding method further comprising:
a step of generating a fourth magnetic field applied to the magnet to guide the medical device; and
a step of controlling an output of the first magnetic field and an output of the second magnetic field according to a value of mutual inductance between at least two magnetic fields among the generated first magnetic field, second magnetic field, third magnetic field, and fourth magnetic field.

37. A position detecting method according to claim 24, wherein an axial-direction magnetic field is generated along a substantially cylindrical surface surrounding the detection space, in an axial direction of the substantially cylindrical surface.

38. A position detecting method according to claim 24, wherein the second magnetic field is generated along a substantially cylindrical surface surrounding the detection space, in one radial direction of the substantially cylindrical surface.

39. A position detecting method according to claim 24, further comprising a step of selecting a magnetic field to be generated from among the first magnetic field and the second magnetic field according to at least one of position and orientation of the detected object.

40. A position detecting method according to claim 24, further comprising a step of controlling an output of the first magnetic field and an output of the second magnetic field according to a value of mutual inductance between the generated first magnetic field and second magnetic field.

41. A position detecting method according to claim 24, wherein the generated first magnetic field and second magnetic field are synchronized with each other.

42. A medical device guiding method comprising:
a position detecting method according to claim 24,
wherein the detected object is a medical device provided with the circuit including the built-in coil and a magnet,
the medical device guiding method further comprising:
a step of generating a fourth magnetic field applied to the magnet to guide the medical device; and
a step of controlling an output of the first magnetic field and an output of the second magnetic field according to a value of mutual inductance between at least two magnetic fields among the generated first magnetic field, second magnetic field, and fourth magnetic field.

* * * * *